United States Patent [19]

Waerve

[11] 4,341,279
[45] Jul. 27, 1982

[54] MOBILE X-RAY APPARATUS

[75] Inventor: Hans Waerve, Sollentuna, Sweden

[73] Assignee: Siemens Aktiengesellschaft, Berlin & Munich, Fed. Rep. of Germany

[21] Appl. No.: 163,712

[22] Filed: Jun. 27, 1980

Related U.S. Application Data

[63] Continuation of Ser. No. 940,377, Sep. 7, 1978, abandoned.

[30] Foreign Application Priority Data

Oct. 3, 1977 [DE] Fed. Rep. of Germany ... 7730536[U]

[51] Int. Cl.³ .............................................. B62D 3/02
[52] U.S. Cl. .................................. 180/19 S; 180/253; 280/269
[58] Field of Search ................. 180/19 R, 19 S, 19 H, 180/253; 280/93, 95 R, 267, 269; 250/523

[56] References Cited

U.S. PATENT DOCUMENTS

| | | | |
|---|---|---|---|
| 3,068,019 | 12/1962 | Ulinski | 280/93 |
| 3,163,250 | 12/1964 | Gibson | 180/253 |
| 3,181,640 | 5/1965 | Goodacre et al. | 180/19 R |
| 3,790,805 | 2/1974 | Forderaro | 250/523 |
| 3,836,177 | 9/1974 | Heidt | 280/95 R |
| 4,020,918 | 5/1977 | Houskamp et al. | 180/98 |
| 4,052,082 | 10/1977 | Jones et al. | 280/87.02 R |
| 4,063,612 | 12/1977 | Weiss | 180/19 S |
| 4,113,042 | 9/1978 | Vaill | 180/19 R |

FOREIGN PATENT DOCUMENTS 2026953   2/1980   United Kingdom ............... 280/442

Primary Examiner—Joseph F. Peters, Jr.
Assistant Examiner—Donn McGiehan
Attorney, Agent, or Firm—Hill, Van Santen, Steadman, Chiara & Simpson

[57] ABSTRACT

The disclosure relates to a mobile, motor-transportable x-ray apparatus comprising a carriage and wheels; in the illustrated embodiment, a rear wheel assembly is both driven and steerable. The steerable wheel, or the steerable wheels, are connected with a rearwardly extending manually operable steering device which is to be turned to the left or right to direct the apparatus to the left or right, respectively, as it is driven in the forward direction.

1 Claim, 2 Drawing Figures

MOBILE X-RAY APPARATUS

This is a continuation of application Ser. No. 940,377, filed Sept. 7, 1978, and now abandoned.

BACKGROUND OF THE INVENTION

The invention relates to a mobile, motor-transportable x-ray apparatus comprising a carriage and comprising wheels, one or more of which is driven and one or more of which is steerable.

An x-ray apparatus of this type is known from the brochure "Kondiamobil 125" of the Siemens firm. In this apparatus, the motor-driven wheels are large and the steerable wheels are comparatively small. The driven wheels are not capable of being steered. On account of the small wheels, it is difficult to transport the x-ray apparatus over obstacles, for example thresholds. Moreover, the x-ray apparatus can be sterred only with difficulty due to the large wheels. The steerable wheels are here freely rotatable about vertical axes, and adjust themselves corresponding to the respective transport direction. However, they are unable to determine the transport direction.

SUMMARY OF THE INVENTION

The object underlying the invention consists in producing a mobile x-ray generator which can be readily manually steered.

This object is achieved in accordance with the invention by virtue of the fact that the steerable wheel, or the steerable wheels, are connected to a manually operable steering device. The user is thus enabled to determine the transport direction by means of the steering device via the steerable wheel, or the steerable wheels, such that an effortless steering is guaranteed.

In an advantageous embodiment of the invention, it is proposed that all wheels be of equal size. What is achieved thereby is that the x-ray apparatus can be more readily transported over obstacles than the known x-ray apparatus.

A particularly expedient further development of the invention is to be found in that the steerable wheels are motor-driven. A particularly simple control of the x-ray apparatus is thereby possible. In addition, the steering of the x-ray apparatus requires very little force. This is the case especially when one motor is associated with each steerable wheel.

In an expedient further development, the steering bar of the steering device can be foldable into a recess of the carriage housing such that it does not cause interference during operation with the x-ray apparatus.

The invention is explained in further detail in the following on the basis of a sample embodiment illustrated in the accompanying sheet of drawings; and other objects, features and advantages will be apparent from this detailed disclosure and from the appended claims.

DETAILED DESCRIPTION

Figure 2:
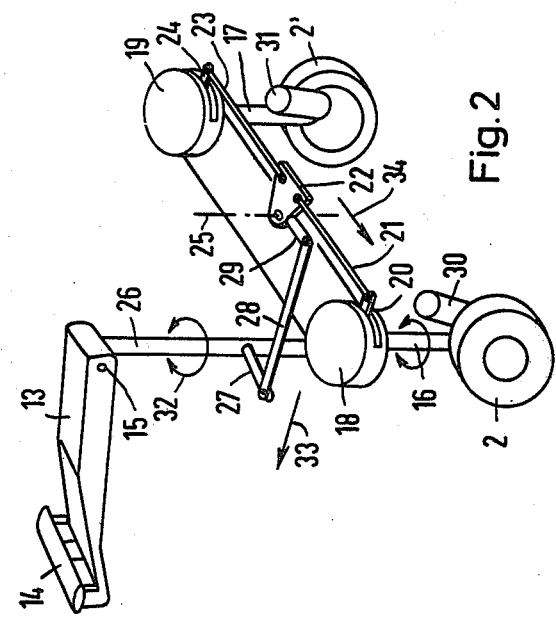
FIG. 2 illustrates exemplary details of the steering system for an x-ray apparatus according to FIG. 1.
Figure 1:
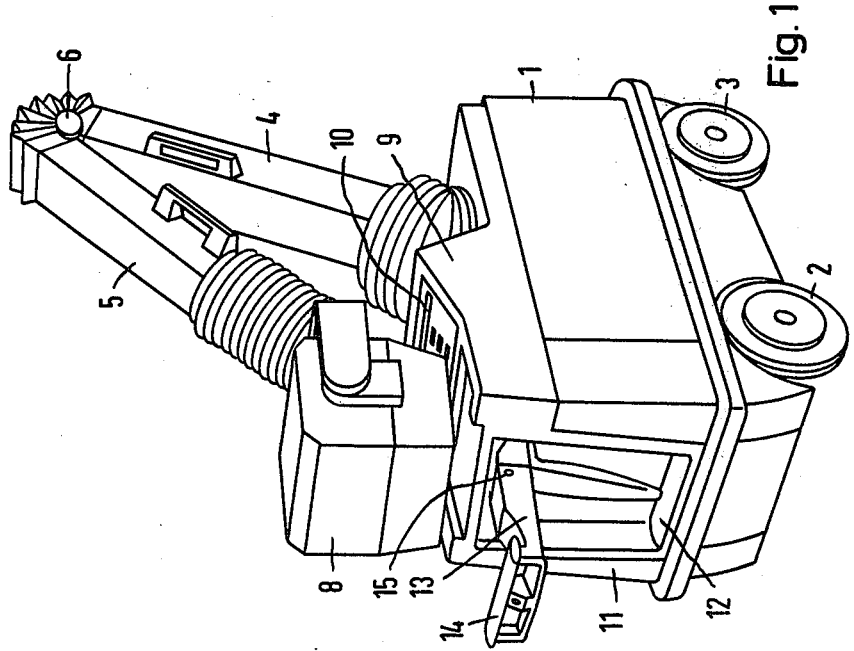
FIG. 1 illustrates a mobile x-ray apparatus in accordance with the invention.

In FIG. 1, a carriage 1 is illustrated which is provided with four wheels of which only two wheels 2, 3 are visible. Rear wheel 2 and the opposite rear wheel 2', only visible in FIG. 2, are steerable with means to be described later. On the upper side of carriage 1, there is arranged a pivotally mounted carrier arm 4 whose free end is connected in an articulated fashion with a second carrier arm 5 by means of an axis 6. The carrier arm 5, in turn, bears at its free end an x-ray tube assembly including a collimator arranged in a housing 8.

There is also disposed in housing 8 the high voltage generator whereas the switching and control elements are arranged on carriage 1 in and on its housing. Carriage 1 manifests at its upper side an obliquely angled stage 9 on which is arranged an operating panel 10 for the purpose of adjusting the photographic parameters. At the rear end of carriage 1, the carriage housing has an end wall 11 with a recess 12 from which a steering bar 13 with a handle 14 projects, the handle 14 being laterally movable while in the active position shown to serve the purpose of steering the motor-driven wheels 2, 2'. There is arranged on handle 14 a non-illustrated operating button for the purpose of switching on and off the motor-driven wheels 2, 2'. The steering bar 13 is pivotally mounted about an axis 15 so that it can be folded into the recess 12.

FIG. 2 illustrates that the steering bar 13 is capable of pivoting (or steering) the wheels 2, 2' about vertical axes via rods. The wheels 2, 2' are rotatably mounted on vertical supports 16, 17. The vertical supports 16, 17 are mounted for rotation about their respective longitudinal axes on bearings 18, 19. The wheels 2, 2' are interconnected via supports 16, 17 by means of the rods 20, 21, connected in an articulated fashion, and by means of the rods 23, 24, likewise connected in an articulated fashion, and by means of the triangularly-shaped sheet metal plate 22 which connects the rods 21 and 23 in an articulated fashion. The sheet metal plate 22 is pivotally mounted about an axis 25. The sheet metal plate 22 is, moreover, connected with the steering bar 13 via a shaft 26 which is rotatable about its axis, and via rods 27, 28, 29. The rods 27 and 29 are fixed to the shaft 26 and to the sheet metal plate 22, respectively. Rod 28 is connected with rods 27 and 29 in a steerable fashion. FIG. 2 further illustrates that a respective motor 30, 31, is associated with each steerable wheel 2, 2'.

Pursuant to manual turning of the steering bar 13, the shaft 26 rotates about its axis in the direction of double headed arrow 32 and actuates rod 28 (e.g. in the direction of arrow 33 for a left turn) by means of rod or arm 27. The sheet metal plate 22 is thus rotated about axis 25 by means of rod 29, with the result that rods 21 and 23 become displaced (e.g. in the direction of arrow 34) in such a manner that the wheels 2, 2' are turned to steer the apparatus in the turning direction of steering rod 13 via rods 20, 24 and via supports 16, 17. If the steering rod is pivoted in the opposite direction, the rods move in a correspondingly opposite manner, and the wheels are turned in conformity with this pivoting movement.

It will be apparent that many modifications and variations may be effected without departing from the scope of the novel concepts and teachings of the present invention.

I claim as my invention:

1. In a four-wheeled cart suitable for supporting an X-ray apparatus thereon, with two powered wheels at a selected end of the cart and a steering handle rotatably attached to the selected end of the cart, an improvement wherein:

each of said four wheels has substantially the same diameter;

each of said powered wheels has a motor connected thereto;

and an improved steering device comprising:

first and second vertical members rotatably connected to the powered wheels;

first and second spaced apart bearings mounted on the cart, each said bearing rotatably supports one of said vertical members for rotation about a vertical axis adjacent each respective powered wheel;

first and second rigid elongated rods, each said rod is pivotably connected between one of said vertical members and an interconnection plate mounted on the cart for essentially only rotation about a fixed vertical axis;

an articulated linkage connected only to a rotatable section of the steering handle and said interconnection plate whereby rotary movement of the steering handle in a first arcuate direction only rotates said interconnection plate a corresponding amount which in turn rotates each powered wheel about said adjacent vertical axis in the first arcuate direction and rotary movement of the steering handle opposite said first arcuate direction correspondingly only rotates said interconnection plate a corresponding amount which in turn rotates each powered wheel about said adjacent vertical axis in the opposite arcuate direction.

* * * * *